United States Patent
Wu et al.

(10) Patent No.: US 7,815,856 B2
(45) Date of Patent: Oct. 19, 2010

(54) STORAGE CONTAINER FOR DETECTING PRESENCE OF CHECMICAL ELEMENTS

(75) Inventors: Kwang-Chen Wu, Taipei (TW); Long-Sheng Yeou, Hsinchu (TW)

(73) Assignee: Taiwan Semiconductor Manufacturing Co., Ltd., Hsin-Chu (TW)

( * ) Notice: Subject to any disclaimer, the term of this patent is extended or adjusted under 35 U.S.C. 154(b) by 1184 days.

(21) Appl. No.: 11/419,767

(22) Filed: May 23, 2006

(65) Prior Publication Data

US 2007/0275468 A1    Nov. 29, 2007

(51) Int. Cl.
*G01N 31/22* (2006.01)

(52) U.S. Cl. .............................. 422/58; 422/102; 436/2; 436/3

(58) Field of Classification Search .................. 422/56, 422/58, 61; 436/1–3
See application file for complete search history.

(56) References Cited

U.S. PATENT DOCUMENTS

| | | | |
|---|---|---|---|
| 5,836,736 A | 11/1998 | Thompson et al. | |
| 5,942,438 A | * 8/1999 | Antonoplos et al. | ............ 436/1 |
| 6,370,406 B1 | 4/2002 | Wach et al. | |
| 6,662,950 B1 | 12/2003 | Cleaver | |
| 6,727,494 B2 | 4/2004 | Lin | |
| 6,960,257 B2 | 11/2005 | Thompson et al. | |

* cited by examiner

*Primary Examiner*—Lyle A Alexander
(74) *Attorney, Agent, or Firm*—Thomas, Kayden, Horstemeyer & Risley

(57) ABSTRACT

A container having an indicator for detecting the presence of chemical elements is provided. In one embodiment, the container comprises a cavity therein for receiving an article having a first metallic element, the cavity being substantially sealed from a surrounding environment outside the container. An indicator is disposed within the sealed cavity, the indicator having a second metallic element with a standard potential less than the standard potential of the first metallic element, whereby a change in state of the second metallic element alerts an operator to the presence of a predetermined chemical element within the container.

13 Claims, 6 Drawing Sheets

Standard Reduction Potentials in Aqueous Solution at 25 °C

| Cathode (Reduction) Half-Reaction | Standard Potential E° (volts) |
|---|---|
| $Li^+(aq) + e^- \rightarrow Li(s)$ | -3.04 |
| $K^+(aq) + e^- \rightarrow K(s)$ | -2.92 |
| $Ca^{2+}(aq) + 2e^- \rightarrow Ca(s)$ | -2.76 |
| $Na^+(aq) + e^- \rightarrow Na(s)$ | -2.71 |
| $Mg^{2+}(aq) + 2e^- \rightarrow Mg(s)$ | -2.38 |
| $Al^{3+}(aq) + 3e^- \rightarrow Al(s)$ | -1.66 |
| $2H_2O(l) + 2e^- \rightarrow H_2(g) + 2OH^-(aq)$ | -0.83 |
| $Zn^{2+}(aq) + 2e^- \rightarrow Zn(s)$ | -0.76 |
| $Cr^{3+}(aq) + 3e^- \rightarrow Cr(s)$ | -0.74 |
| $Fe^{2+}(aq) + 2e^- \rightarrow Fe(s)$ | -0.41 |
| $Cd^{2+}(aq) + 2e^- \rightarrow Cd(s)$ | -0.40 |
| $Ni^{2+}(aq) + 2e^- \rightarrow Ni(s)$ | -0.23 |
| $Sn^{2+}(aq) + 2e^- \rightarrow Sn(s)$ | -0.14 |
| $Pb^{2+}(aq) + 2e^- \rightarrow Pb(s)$ | -0.13 |
| $Fe^{3+}(aq) + 3e^- \rightarrow Fe(s)$ | -0.04 |
| $2H^+(aq) + 2e^- \rightarrow H_2(g)$ | 0.00 |
| $Sn^{4+}(aq) + 2e^- \rightarrow Sn^{2+}(aq)$ | 0.15 |
| $Cu^{2+}(aq) + e^- \rightarrow Cu^+(aq)$ | 0.16 |
| $ClO_4^-(aq) + H_2O(l) + 2e^- \rightarrow ClO_3^-(aq) + 2OH^-(aq)$ | 0.17 |
| $AgCl(s) + e^- \rightarrow Ag(s) + Cl^-(aq)$ | 0.22 |
| $Cu^{2+}(aq) + 2e^- \rightarrow Cu(s)$ | 0.34 |
| $ClO_3^-(aq) + H_2O(l) + 2e^- \rightarrow ClO_2^-(aq) + 2OH^-(aq)$ | 0.35 |
| $IO^-(aq) + H_2O(l) + 2e^- \rightarrow I^-(aq) + 2OH^-(aq)$ | 0.49 |
| $Cu^+(aq) + e^- \rightarrow Cu(s)$ | 0.52 |
| $I_2(s) + 2e^- \rightarrow 2I^-(aq)$ | 0.54 |
| $ClO_2^-(aq) + H_2O(l) + 2e^- \rightarrow ClO^-(aq) + 2OH^-(aq)$ | 0.59 |
| $Fe^{3+}(aq) + e^- \rightarrow Fe^{2+}(aq)$ | 0.77 |
| $Hg_2^{2+}(aq) + 2e^- \rightarrow 2Hg(l)$ | 0.80 |
| $Ag^+(aq) + e^- \rightarrow Ag(s)$ | 0.80 |
| $Hg^{2+}(aq) + 2e^- \rightarrow Hg(l)$ | 0.85 |
| $ClO^-(aq) + H_2O(l) + 2e^- \rightarrow Cl^-(aq) + 2OH^-(aq)$ | 0.90 |
| $2Hg^{2+}(aq) + 2e^- \rightarrow Hg_2^{2+}(aq)$ | 0.90 |
| $NO_3^-(aq) + 4H^+(aq) + 3e^- \rightarrow NO(g) + 2H_2O(l)$ | 0.96 |
| $Br_2(l) + 2e^- \rightarrow 2Br^-(aq)$ | 1.07 |
| $O_2(g) + 4H^+(aq) + 4e^- \rightarrow 2H_2O(l)$ | 1.23 |
| $Cr_2O_7^{2-}(aq) + 14H^+(aq) + 6e^- \rightarrow 2Cr^{3+}(aq) + 7H_2O(l)$ | 1.33 |
| $Cl_2(g) + 2e^- \rightarrow 2Cl^-(aq)$ | 1.36 |
| $Ce^{4+}(aq) + e^- \rightarrow Ce^{3+}(aq)$ | 1.44 |
| $MnO_4^-(aq) + 8H^+(aq) + 5e^- \rightarrow Mn^{2+}(aq) + 4H_2O(l)$ | 1.49 |
| $H_2O_2(aq) + 2H^+(aq) + 2e^- \rightarrow 2H_2O(l)$ | 1.78 |
| $Co^{3+}(aq) + e^- \rightarrow Co^{2+}(aq)$ | 1.82 |
| $S_2O_8^{2-}(aq) + 2e^- \rightarrow 2SO_4^{2-}(aq)$ | 2.01 |
| $O_3(g) + 2H^+(aq) + 2e^- \rightarrow O_2(g) + H_2O(l)$ | 2.07 |
| $F_2(g) + 2e^- \rightarrow 2F^-(aq)$ | 2.87 |

FIG. 1

STORAGE CONTAINER FOR DETECTING PRESENCE OF CHECMICAL ELEMENTS

BACKGROUND

The present invention relates generally to storage containers for transporting articles, and particularly, to storage containers used in semiconductor fabrication facilities for transporting or storing wafers, and more particularly to storage containers having an indicator for detecting corrosive chemical elements.

A wafer has multiple microchips on its surface, and each chip has literally millions of devices and interconnection circuitry that are highly sensitive to contamination. As the feature size on a chip shrinks to accommodate higher performance and denser circuitry and the use of corrosion-prone copper, the need to control surface contamination becomes more critical. Contamination, which can come from many sources during wafer fabrication, such as particles, metals, and electrostatic discharge (ESD) often leads to a defective chip. The wafer fabrication process comprises many steps, such as patterning, deposition, etching, implantation or diffusion of metallic layers, dielectric layers or impurity elements on a semiconductor substrate. One such contamination comes from corrosive trace elements in the environment. Metal layers on a wafer exposed to the environment will often react with some trace elements in the environment such as, for example fluorine, chlorine, sulfur, and produce defects such as corrosion, metal pad discoloration, pad crystal defect, and metal fuse corrosion. For example, when copper corrosion occurs, the adhesion of the copper layer with other layers such as an inter-metal dielectric (IMD) of oxide is greatly affected. Killer defects are those causes of failure where the chip on the wafer fails during electrical test. Failure at electrical test results in a yield loss, causing the defective die on the wafer to be scrapped (thrown away) at a significant cost to the chip manufacturer. As device critical dimensions decrease, the problem of contamination becomes ever critical.

Until now, the preventative method is to store wafers in a controllable environment such as cleanrooms and minienvironments purged with an inert-gas like nitrogen, and to monitor the amount of trace elements with expensive measurement tools. However, corrosive trace elements come not only from the cleanroom environment, but may also come from the wafer container and wafer cassette themselves due to chemical outgassing or from residues left on the front side or backside of the wafer during IC processing. Storage of wafers in nitrogen-purged cleanrooms or minienvironments can only prevent external contamination but cannot stop contamination from within the wafer container itself.

For these reasons and other reasons that will become apparent upon reading the following detailed description, there is a need for a storage container for detecting the presence of corrosive chemical elements.

SUMMARY

The present invention is directed to a container having an indicator for detecting the presence of chemical elements. In one embodiment, the container comprises a cavity therein for receiving an article having a first metallic element, the cavity being substantially sealed from a surrounding environment outside the container. An indicator is disposed within the sealed cavity, the indicator having a second metallic element with a standard potential less than the standard potential of the first metallic element, whereby a change in state of the second metallic element alerts an operator to the presence of a predetermined chemical element within the container.

BRIEF DESCRIPTION OF THE DRAWINGS

The features, aspects, and advantages of the present invention will become more fully apparent from the following detailed description, appended claims, and accompanying drawings in which:

FIG. 1 is a table showing standard reduction potentials of certain metals.

DETAILED DESCRIPTION

Figure 2A:
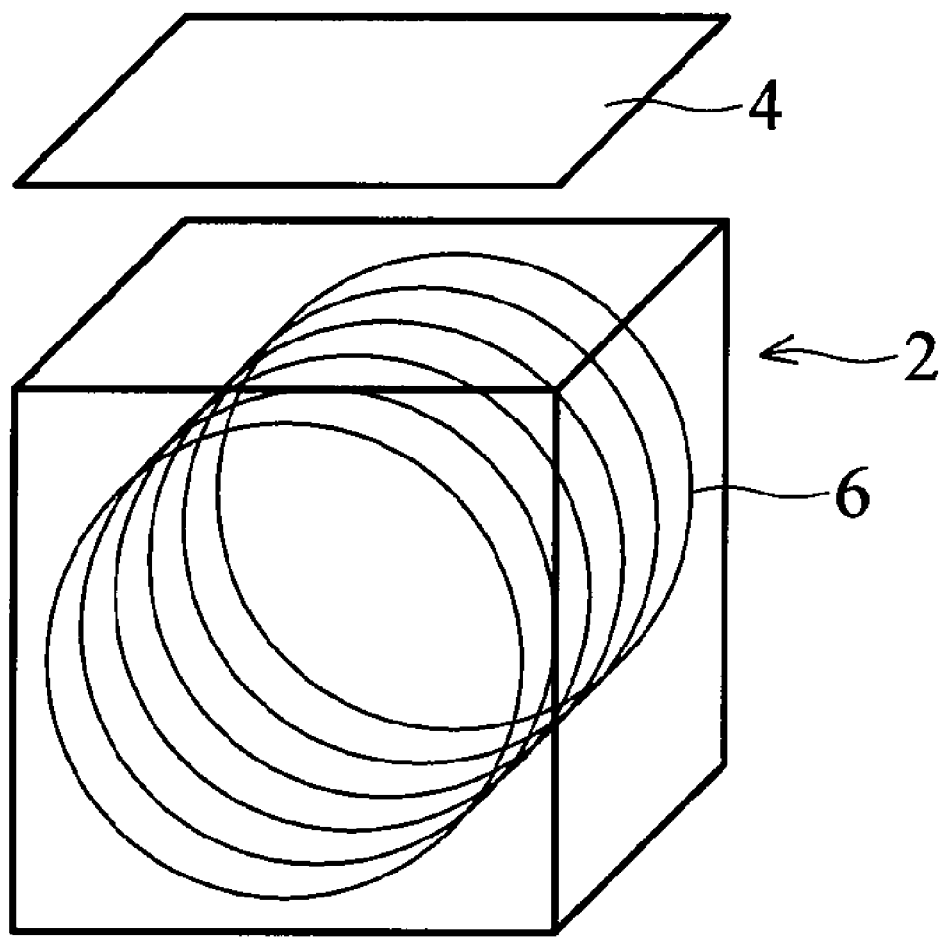
FIG. 2A is a perspective view of a typical conventional IC wafer container.

In the following description, numerous specific details are set forth to provide a thorough understanding of the present invention. However, one having an ordinary skill in the art will recognize that the invention can be practiced without these specific details. In some instances, well-known structures and processes have not been described in detail to avoid unnecessarily obscuring the present invention.

The present invention discloses a storage container having an indicator therein for detecting the concentration of various chemical elements, such as corrosive chemicals within the container. While the present invention chemical element indicator storage container can be used for storing and transporting any type of articles, it is particularly suited, but not limited, to the storing and transportation of wafers that have metal layers (e.g. copper, aluminum) deposited thereon and thus, are susceptible to corrosion and resulting damages to the device structure fabricated. It is understood that metals, which are frequently found to be susceptible to corrosion under normal atmospheric and ambient conditions include, but are not limited to, copper, aluminum, iron, brass, silver, and alloys of these metals.

Reference will now be made in detail to the present preferred embodiments of the present invention, examples of which are illustrated in the accompanying drawings.

Corrosion involves the deterioration of a material as it reacts with its environment. The corrosion process is usually electrochemical in nature and involves the chemical processes of oxidation and reduction. It is a natural process that commonly occurs because unstable materials, such as active metals want to return to a more stable compound. For example, some metals, such as gold, silver, and platinum can be found in the earth in their natural, metallic state and they have little tendency to corrode. Iron, on the other hand, is a moderately active metal and corrodes readily in the presence of water. The natural state of iron is iron oxide and the most common iron ore is Hematite with a chemical composition of $Fe_2O_3$. Rust, the most common corrosion product of iron, also has a chemical composition of $Fe_2O_3$.

As is understood by those skilled in the art, the table of standard reduction potentials in FIG. 1 is a ranking of metallic elements, or metals with respect to their inherent reactivity and can be used to compare the corrosive power or reducing power of a metal. The standard reduction potentials are customarily determined at solute concentrations of 1 Molar, gas pressures of 1 atmosphere, and a standard temperature, which is usually 25° C. The standard cell potential is denoted by a degree E sign as a superscript and the standard reduction potentials for the various metals are measured against a standard hydrogen electrode, which is assigned a potential of zero volts. The most noble metal (e.g. inactive or inert metal) is at the bottom of the table and has the highest positive standard potential. The most active metal is at the top and has the most negative standard potential. The values shown in the table are reduction potentials, so lithium at the top of the list has the most negative number, indicating that it is the strongest reducing agent.

In accordance with teachings of the present invention, it is the chemical reaction resulting from a difference in potential of metals that can be used to gauge the corrosive or reducing power of a particular metallic element. An example will illustrate an aspect of this invention. Assume that inside a sealed container contains an article, such as for example a wafer that has thereon a metallic element copper (standard potential=0.34), such as a copper fuse or copper line. If it is desired to determine the presence or concentration of one or more chemical element within the container before these chemical elements react with copper, the metallic element silver chloride (AgCl) from FIG. 1 may be used as an indicator. The chemical element may be a corrosive element and may include, for example, chlorine, fluorine, or sulfur. From FIG. 1, an indicator having a material with a standard potential equal or less than that of copper will exhibit equal or higher corrosive behavior than copper under a standard atmosphere. AgCl has a standard potential of 0.22, which is lower than the standard potential of copper (0.34) and therefore exhibits a stronger corrosive behavior than copper under standard atmosphere. Consequently, AgCl will react sooner and therefore corrode faster than copper. An operator seeing a change in state of the AgCl substance can be alerted to the presence of the chemical element. The AgCl will react with this chemical element and the change in state of the AgCl will occur before the change in state of the copper thereby alerting the operator to take appropriate action, such as removing the article (e.g. wafer) from container to avoid copper corrosion or replacing the container with another or same container but having a new indicator therein for storing or transporting the wafer. In one embodiment of the present invention, the change in state of the metallic element (AgCl) is a change in color or discoloration of the metallic element. The color change provides an indication to the operator to the presence of the chemical element. In another embodiment, a change in state of the metallic element is a decay of the metallic element and this decay can alert the operator of the presence of the chemical element. In one embodiment, the decay may be manifested by oxidation, pitting, tarnishing, or mottling. In another embodiment, the indicator may comprise of one or more layers, made from different materials or the same material in a multilayer structure, or made from a metallic compound or alloy.

In another embodiment of the present invention, if it is desired to determine copper corrosion in a shorter period of time or predict whether a given reduction reaction (e.g., corrosion) will be spontaneous, a metallic element having a standard potential lower than that of AgCl may be used. For instance, perchlorate ($ClO_4^-$) may be used instead of AgCl because $ClO_4^-$ has a standard potential of 0.17 that is lower than that of AgCl; $ClO_4^-$ will react sooner and therefore corrode faster than AgCl. Furthermore, stannum ($Sn^{4+}$) that has a standard potential lower than that of $ClO_4^-$ may be used instead of $ClO_4^-$ if it is desired to determine copper corrosion in an even shorter period of time. Each successive chemical element having a lower standard potential than the previous one will alert the operator of a chemical reaction in a correspondingly shorter period of time.

In another exemplary illustration, assume that inside a sealed container contains an article, such as for example a wafer that has thereon a metallic element aluminum (standard potential=−1.66), such as an aluminum line. If it is desired to determine the presence of one or more chemical element (e.g., chlorine, fluorine, or sulfur) within the container before these chemical elements react with aluminum, the metallic element magnesium ($Mg^{2+}$) may be used as an indicator. From FIG. 1, $Mg^{2+}$ has a standard potential of −2.38, which is lower than the standard potential of aluminum (−1.66) and therefore exhibits a stronger corrosive behavior than aluminum under standard atmosphere. Consequently, $Mg^{2+}$ will react sooner and therefore corrode faster than aluminum. An operator seeing a change in state of the $Mg^{2+}$ substance can be alerted to the presence of the chemical element. The $Mg^{2+}$ will react with this chemical element and the change in state of the $Mg^{2+}$ (e.g., change in color, change in chemical composition) will occur before the change in state of the aluminum thereby alerting the operator to take appropriate action, such as removing the article from container to avoid aluminum corrosion.

The chemical element indicator may be a thin layer that is attached or fastened to a strip, adhesive, or tape or any other suitable material for placement inside of a storage container, such as a wafer storage container. In one embodiment of the present invention, the chemical element indicator 8 has a thickness of about 0.1 μm to about 200 μm. In one embodiment, the chemical element indicator 8 has a thickness of from about 1 μm to about 100 μm. It is understood that any suitable manner of attaching the chemical element indicator to the material may be employed and that there is no limit as to the physical type of material, which may be used. As shown in FIG. 2A, the wafer storage container 2 can be constructed with a container body that has a front wall, a back wall, a left-side wall, a right-side wall, and a bottom wall defining a cavity therein for receiving at least a wafer 6, and a top wall 4 for forming a sealed cavity therein. Wafer storage container 2 may be a standard mechanical interface (SMIF) pod or a front opening shipping box (FOSB). The SMIF pod is used not only in transporting wafer cassettes between various processing stations, but also in storing wafers in cassettes waiting to be processed. Wafer storage container 2 is preferably made of a transparent material so that the operator may see the content inside and the chemical element indicator. It is understood that the strip upon which the chemical element indicator is attached thereto is a consumable item that should be replenished, or replaced, disposed, or recycled after a pre-determined time of usage.

Figure 2B:
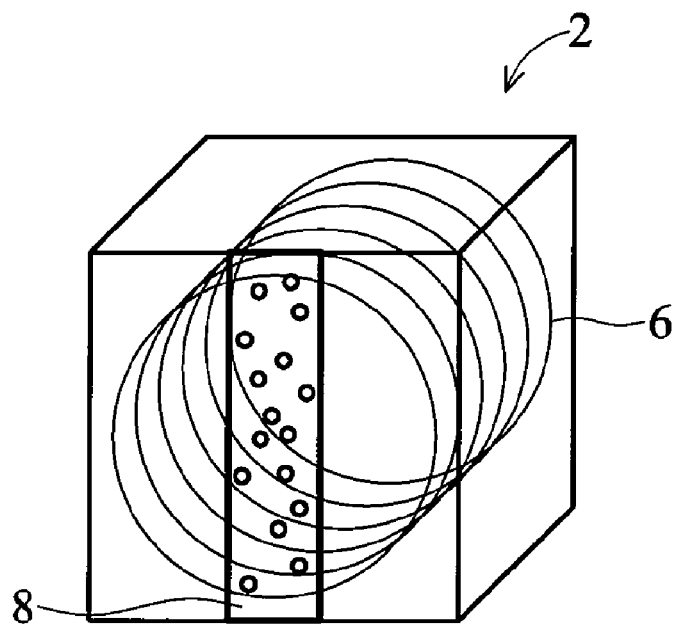
FIG. 2B is a perspective view of a wafer container having a chemical element indicator placed on a front wall of the container according to one embodiment of the present invention.
Figure 2C:
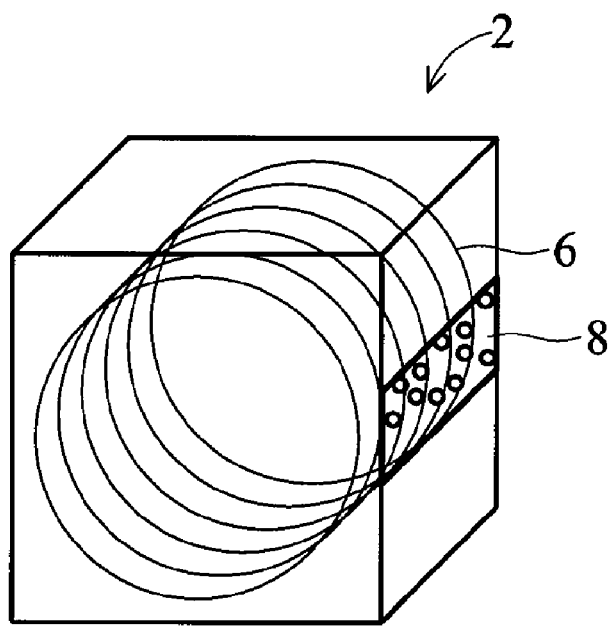
FIG. 2C is a perspective view of a wafer container having a chemical element indicator placed on a sidewall of the container according to one embodiment of the present invention.
Figure 2D:
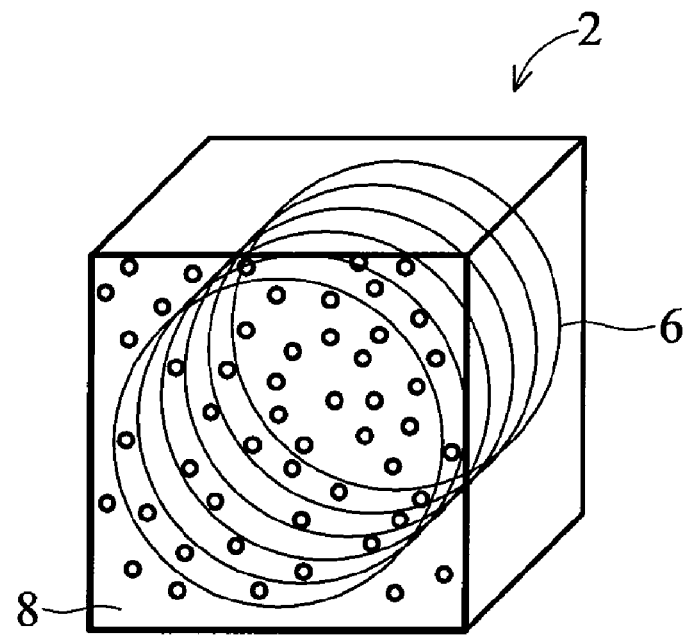
FIG. 2D is a perspective view of a wafer container having a chemical element indicator placed on a front wall of the container according to one embodiment of the present invention.
Figure 2E:
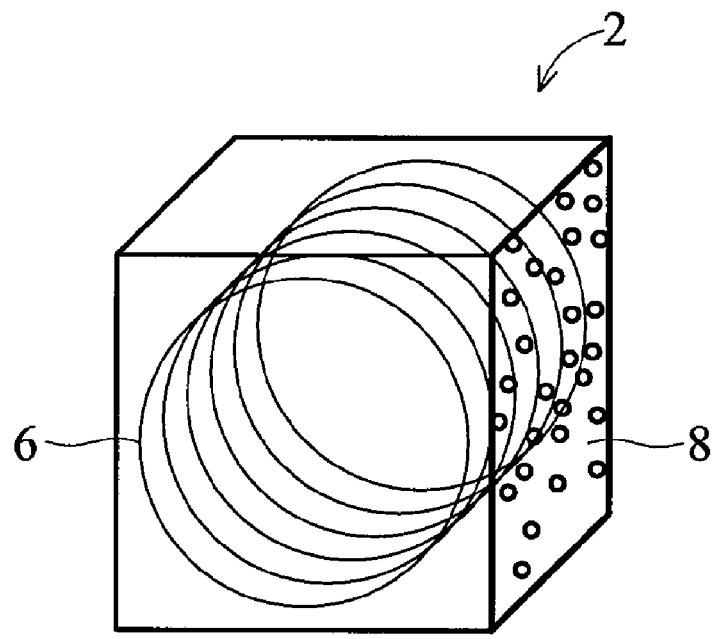
FIG. 2E is a perspective view of a wafer container having a chemical element indicator placed on a sidewall of the container according to one embodiment of the present invention.
Figure 2F:
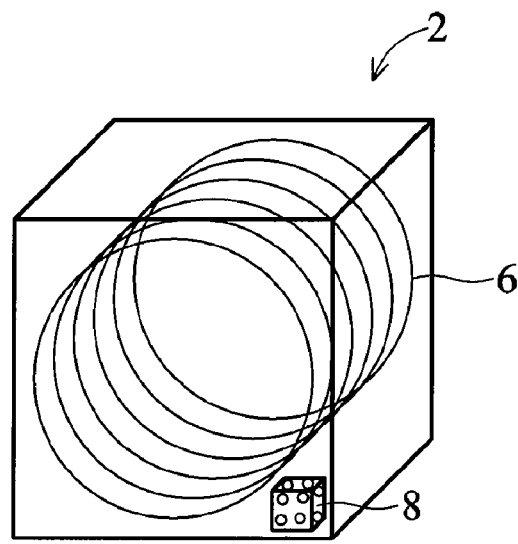
FIG. 2F is a perspective view of a wafer container having a chemical element indicator placed inside the container according to one embodiment of the present invention.
Figure 2G:
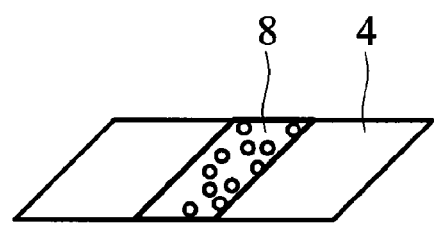
FIG. 2G is a perspective view of a wafer container cover having a chemical element indicator placed thereunder according to one embodiment of the present invention.
Figure 2H:
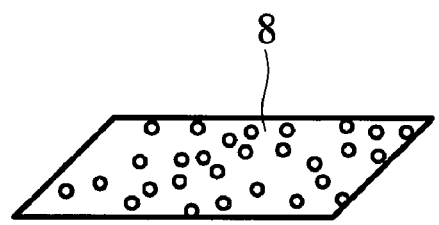
FIG. 2H is a perspective view of a wafer container cover having a chemical element indicator placed thereunder according to one embodiment of the present invention.
Figure 2I:
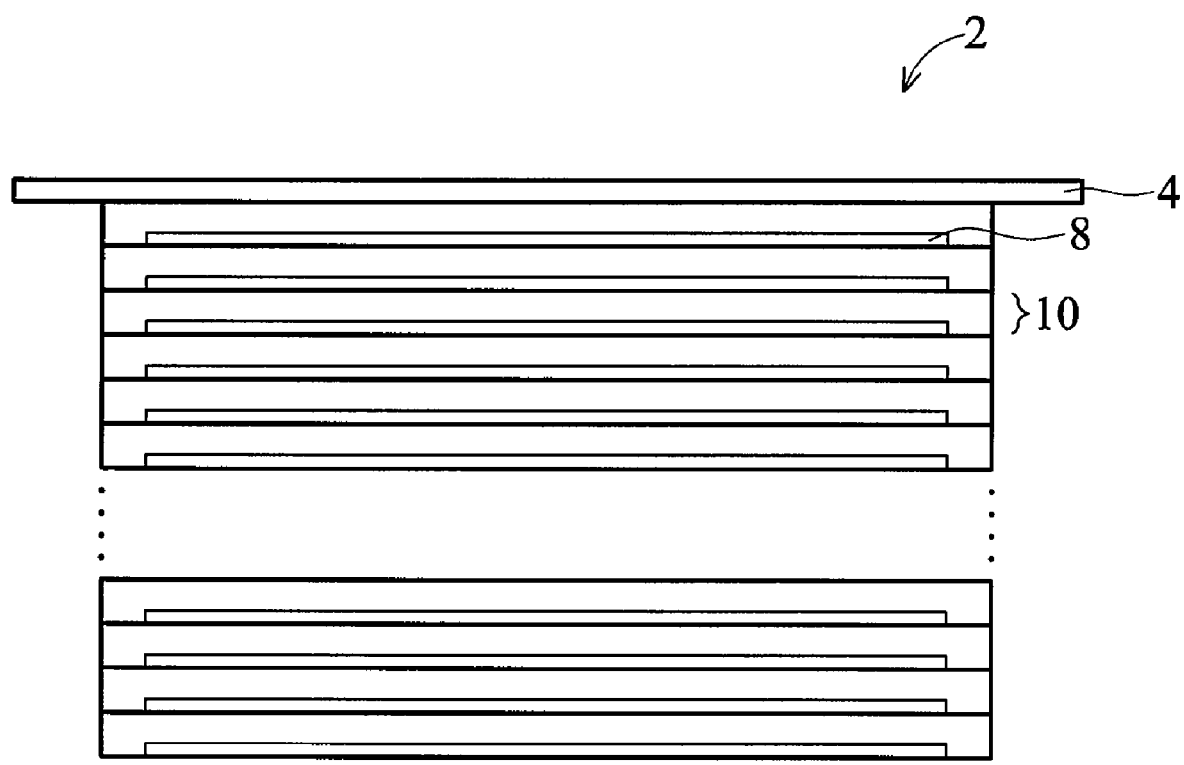
FIG. 2I is a front view of a wafer container with a plurality of chemical element indicators placed within slots of the wafer according to one embodiment of the present invention.

The chemical element indicator 8 may be placed on the inside front wall of container 2 (FIGS. 2B and 2D); on a inside sidewall (FIGS. 2C and 2E); or on the inside container cover 4 (FIGS. 2G and 2H). As shown in FIG. 2F, chemical element indicator 8 may also be contained in the cavity of container 2. FIG. 2I shows chemical element indicators 8 placed in slots 10 of container 2. The wafers (not shown) are generally seated within slots 10 but the wafers are not in contact with the chemical element indicators 8.

It is to be understood that the invention of the present invention is not limited to an indicator in a storage container for detecting the concentration of corrosive chemicals therein, but also to a sacrificial substance for reacting with the corrosive chemical prior to reaction with the metallic layers on the wafer. In other words, the corrosive chemical can successfully consume the sacrificial substance inside the container before it consumes the metallic layers and/or reduce the amount of corrosive chemicals that would otherwise consume the metallic layer.

Further, the present invention describes a method of storing or transporting a wafer in a container having a corrosion indicator therein for preventing corrosion on metal layers of the wafer. In one embodiment, during wafer fabrication, after a fuse repairing process where one or more metal fuses underlying a passivation layer is burned, the wafer with exposed metal fuses is then transferred into a wafer container having a corrosion indicator therein.

In the preceding detailed description, the present invention is described with reference to specifically exemplary embodiments thereof. It will, however, be evident that various modifications, structures, processes, and changes may be made thereto without departing from the broader spirit and scope of the present invention, as set forth in the claims. The specification and drawings are, accordingly, to be regarded as illustrative and not restrictive. It is understood that the present invention is capable of using various other combinations and environments and is capable of changes or modifications within the scope of the inventive concept as expressed herein.

What is claimed is:

1. A container having an indicator, comprising:
    a container having a cavity therein, the cavity being substantially sealed from a surrounding environment outside the container; and
    an indicator disposed within the sealed cavity, the indicator having a metallic element selected from the group consisting of lithium, potassium, calcium, sodium and magnesium, whereby a change in state of the metallic element alerts an operator to a presence of a predetermined chemical element within the container.

2. The container of claim 1, wherein the indicator comprises a strip having a layer of the metallic element thereon.

3. The container of claim 1, wherein the change in state of the metallic element comprises a change in the color of the metallic element.

4. The container of claim 1, wherein the change in state of the metallic element comprises a decay of the metallic element.

5. The container of claim 1, wherein the predetermined chemical element is a corrosive element.

6. The container of claim 5, wherein the corrosive element is a material selected from the group consisting of chlorine, fluorine, and sulfur.

7. A container for wafers having an indicator, the container comprising:
    a container body having a front wall, a back wall, a left-side wall, a right-side wall, and a bottom wall defining a cavity, and a top wall for forming a sealed cavity therein; and
    an indicator disposed within the sealed cavity, the indicator having a metallic element selected from the group consisting of lithium, potassium, calcium, sodium and magnesium, whereby a change in state of the metallic element alerts an operator to a presence of a predetermined chemical element within the container.

8. The container of claim 7, wherein the container is a front opening shipping box (FOSB).

9. The container of claim 7, wherein the indicator comprises a strip having a layer of the second metallic element thereon.

10. The container of claim 7, wherein the change in state of the metallic element comprises a change in the color of the metallic element.

11. The container of claim 7, wherein the change in state of the metallic element comprises a decay of the metallic element.

12. The container of claim 7, wherein the predetermined chemical element is a corrosive element.

13. The container of claim 12, wherein the corrosive element is a material selected from the group consisting of chlorine, fluorine, and sulfur.

\* \* \* \* \*